United States Patent

Suzuki et al.

[11] Patent Number: 5,117,000
[45] Date of Patent: May 26, 1992

[54] PREPARATION OF N-(1-(THIENYL)ALKYL)AMINE DERIVATIVE

[75] Inventors: Hitomi Suzuki; Takuji Ogawa; Hidemitsu Uno, all Ehime; Tetsuo Kitahaba, Osaka; Kouji Kigawa, Osaka; Tomonori Fukamachi, Osaka; Katsuhiko Kitahara, Kyoto, all of Japan

[73] Assignee: Daikin Industries, Ltd., Osaka, Japan

[21] Appl. No.: 499,666

[22] Filed: Mar. 27, 1990

[30] Foreign Application Priority Data

Mar. 31, 1989 [JP] Japan .................... 1-82048

[51] Int. Cl.⁵ ............... C07D 333/32; C07D 333/34
[52] U.S. Cl. ......................... 549/59; 549/65; 549/76; 549/77
[58] Field of Search .................. 549/59, 65, 76, 77

[56] References Cited

U.S. PATENT DOCUMENTS 3,647,775  3/1972  Marguarding et al. ............. 549/3
4,914,215  4/1990  Goodman et al. ................. 549/3

OTHER PUBLICATIONS

Chem. Pharm. Bull., vol. 15, pp. 108–110 (1967).
Chem. Pharm. Bull., vol. 12, pp. 440–444 (1964).
Zaugg (1984) Synthesis, pp. 85–110.

Primary Examiner—Johann Richter
Attorney, Agent, or Firm—Birch, Stewart, Kolasch & Birch

[57] ABSTRACT

N-[1-(Thienyl)alkyl]amine derivative of the formula:

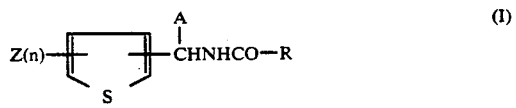

which has excellent herbicidal activity against lowland annual weeds and upland weeds, can be prepared by reacting a thiophen derivative of the formula:

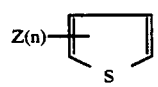

with an aldehyde of the formula:

ACHO and an amide of the formula:

$NH_2—CO—R$ in the presence of formic acid or a mixture of formic acid with phosphoric acid wherein Z is halogen, alkyl or alkoxy group; (n) is 0, 1 or 2; A is hydrogen or alkyl group; R is alkyl group, group of the formula:

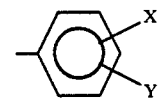

in which X and Y are hydrogen, alkyl group, haloalkyl group, alkoxy group, alkoxymethyl group or halogen, or group of the formula:

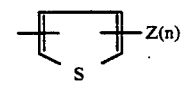

in which Z and (n) are the same as defined above.

16 Claims, No Drawings

PREPARATION OF N-(1-(THIENYL)ALKYL)AMINE DERIVATIVE

BACKGROUND OF THE INVENTION

1. Field of the Invention

The present invention relates to preparation of an N-[1-(thienyl)alkyl]amine derivative, particularly preparation of an N-[1-(thienyl)alkyl]amine derivative through an amidoalkylation reaction in a single stage.

2. Description of the Related Art

An N-[1-(thienyl)alkyl]amine derivative, for example, an N-[1-(thienyl)ethyl]amine derivative has herbicidal activity and is extraordinarily effective against lowland annual weeds such as Echinochloa oryzicola Vasing., Cyperus difformis L., Monochoria vaginalis Presl, Lindernia procumbens Philcox, Rotala indica Koehne and Elatine triandra Schk. and against upland weeds such as Echinochloa frumentacea Link, Digitaria adscendens Henr., Abutilon avicennae Gaertn., Amaranthus viridis L. and Bidens biternata Merr. et Sherff (cf., for example, Japanese Patent Kokai Publication No. 2987/1988).

To prepare an amine derivative of the formula:

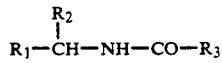

wherein $R_1$ is an organic group, $R_2$ is a hydrogen atom or a lower alkyl group, and $R_3$ is a hydrogen atom or an organic group, which includes the above amine derivative through an amidoalkylation reaction, conventionally the following stepwise process is employed:

(1) $R_3-CO-NH_2 + R_2-CHO$

↓ Acid or base

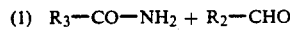

or

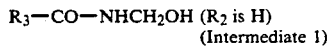

(2) $R_3-CO-NHCH_2OH + R_1H$

↓ Acid

or (2') 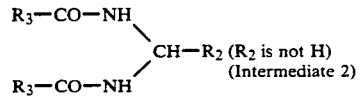

↓ Acid

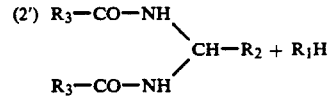

The reason why such stepwise process has been conventionally used is that it does not yield a by-product if the intermediate prepared in the step (1) is isolated and reacted with $R_1H$. When $R_2$ is a hydrogen atom, the stepwise process achieves a high conversion since the intermediate 1 can be isolated. When $R_2$ is not a hydrogen atom, the intermediate 2 other than the intermediate 1 is obtained. In this case, the starting amide is also produced as shown in the step (2'), and therefore the conversion does not exceed 50% even if the reaction of the step (2') proceeds quantitatively.

As a method of preparing said amine derivative, is known the reaction of

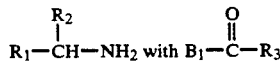

wherein $R_1$, $R_2$ and $R_3$ are the same as defined above, and $B_1$ is a hydroxy group, an alkoxy group or a halogen atom. However, this method needs a separate route to prepare the reactants and is a multistep reaction.

SUMMARY OF THE INVENTION

An object of the present invention is to provide a method of preparing N-[1-(thienyl)alkyl]amine derivative effectively in a single step.

This and other objects are achieved by a method of preparing N-[1-(thienyl)alkyl]amine derivative of the formula:

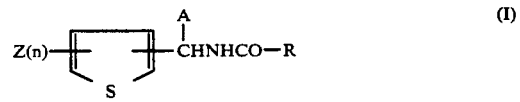 (I)

which comprises reacting a thiophene derivative of the formula:

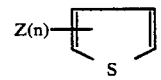

with an aldehyde of the formula:

ACHO and an amide of the formula:

$NH_2-CO-R$ in the presence of formic acid or a mixture of formic acid and phosphoric acid
wherein
  Z is a halogen atom, a lower alkyl group or a lower alkoxy group;
  n is 0, 1 or 2;
  A is a hydrogen atom or an alkyl group having 1 to 8 carbon atoms;
  R is a lower alkyl group, a group of the formula:

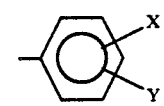

in which X and Y are the same or different and each a hydrogen atom, a straight or branched lower alkyl group (X and Y may form a ring), a straight or branched lower haloalkyl group, a straight or branched lower alkoxy group, a straight or branched lower alkoxymethyl group or a halogen atom, or a group of the formula:

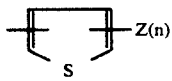

in which Z and n are the same as defined above.

DETAILED DESCRIPTION OF THE INVENTION

Herein, the lower alkyl or alkoxy group is intended to mean one having 1 to 8 carbon atoms, preferably 1 to 4 carbon atoms.

The reaction is effected in the presence of formic acid alone or the mixture of formic acid with phosphoric acid. When formic acid alone is present, it is used in an amount of 200 to 2,000 ml per one mole of the amide. When the mixture of formic acid and phosphoric acid is present, a volume ratio of formic acid to phosphoric acid is 1:1 to 10:1 and the mixture is used in an amount of 200 to 2,000 ml per one mole of the amide. Since the thiophene derivative is unstable in a strong acid such as hydrochloric acid, sulfuric acid and boron trifluoride, such strong acid is not suitable for the reaction.

A molar ratio of the amide to the aldehyde is from 1.0:3.0 to 1.0:1.0, preferably from 1.0:1.0 to 1.0:1.2. A molar ratio of the amide to the thiophene derivative is usually from 1.0:1.0 to 1.0:20, preferably from 1.0:5.0 to 1.0:10.

A reaction temperature is in the range from 0 to 50° C., preferably from 20° to 30° C. When it is higher than 50° C., a by-product yields in a large amount. The reaction time is usually in the range from 30 minutes to 4 hours.

It is not necessary to use a solvent since formic acid or the mixture of formic acid and phosphoric acid acts as the solvent. However, the solvent such as benzene, n-hexane or methylene chloride may be used.

PREFERRED EMBODIMENTS OF THE INVENTION

The present invention is illustrated by following Examples.

EXAMPLE 1

Preparation of N-[1-(2-thienyl)ethyl]-4-isopropylbenzamide:

Thiophene (42 g, 0.5 mol), paraldehyde (4.4 g, 0.033 mole) and 4-isopropylbenzamide (16.3 g, 0.1 mol) were added to a mixture of formic acid (40 ml) and 85% phosphoric acid (20 ml) and stirred at a room temperature for three hours. The reaction mixture was extracted with water (70 ml). An organic phase was washed with water (30 ml) and evaporated to dryness with a rotary evaporator. A residue was recrystallized from carbon tetrachloride/petroleum benzine (1:2) to obtain the entitled compound (20.7 g) as a colorless crystal. Yield: 75.8%. Melting point: 100° C.

EXAMPLE 2

Preparation of N-[1-(5-bromo-2-thienyl)ethyl]-4-isopropylbenzamide:

2-Bromothiophene (8.15 g, 0.05 mol), paraldehyde (2.20 g, 0.017 mol) and 4-isopropylbenzamide (1.63 g, 0.01 mol) were added to formic acid (10 ml) and stirred at a room temperature for three hours. Water (50 ml) was added to the reaction mixture. The mixture was extracted with chloroform (50 ml), subjected to a silica gel column chromatography (eluent: chloroform) and recrystallized from chloroform/petroleum benzine (1:2) to obtain the entitled compound (0.3 g) as a colorless needle-shape crystal. Yield: 8.5%. Melting point: 108° C.

EXAMPLE 3

Preparation of N-[1-(3-bromo-2-thienyl)ethyl]-4-isopropylbenzamide:

3-Bromothiophene (8.15 g, 0.05 mol), paraldehyde (2.20 g, 0.017 mol) and 4-isopropylbenzamide (1.63 g, 0.01 mol) were added to a mixture of formic acid (6 ml) and 85% phosphoric acid (3 ml) and stirred at a room temperature for four hours. Water (50 ml) was added to the reaction mixture. The mixture was extracted with chloroform (50 ml), subjected to a silica gel column chromatography (eluent: chloroform) and recrystallized from chloroform/petroleum benzine (1:2) to obtain the entitled compound (0.6 g) as a colorless plate-shape crystal. Yield: 17.0%. Melting point: 133° C.

EXAMPLE 4

Preparation of N-[1-(5-ethyl-2-thienyl)ethyl]-4-isopropylbenzamide:

2-Ethylthiophene (5.60 g, 0.05 mol), paraldehyde (2.20 g, 0.017 mol) and 4-isopropylbenzamide (1.63 g, 0.01 mol) were added to a mixture of formic acid (6 ml) and 85% phosphoric acid (3 ml) and stirred at a room temperature for four hours. Water (50 ml) was added to the reaction mixture. The mixture was extracted with chloroform (50 ml) and subjected to a silica gel column chromatography (eluent: chloroform) to obtain the entitled compound (2.5 g) as a viscous yellow brown liquid. Yield: 83.1%.

EXAMPLE 5

Preparation of N-[1-(2-thienyl)ethyl]-acetamide:

Thiophene (8.40 g, 0.10 mol), paraldehyde (2.20 g, 0.017 mol) and acetamide (1.18 g, 0.05 mol) were added to a mixture of formic acid (6 ml) and 85% phosphoric acid (3 ml) and stirred at a room temperature for two hours. Water (50 ml) was added to the reaction mixture. The mixture was extracted with chloroform (50 ml), subjected to a silica gel column chromatography (eluent: chloroform) and recrystallized from petroleum benzine to obtain the entitled compound (1.5 g) as a colorless needle-shape crystal. Yield: 88.8 Melting point: 66° C.

EXAMPLE 6

Thiophene (50 mmol), formaldehyde (10 mmol) and 4-isopropylbenzamide (10 mmol) were stirred in formic acid (10 ml) at 20° C. for four hours and treated in the same manner as in Example 2 to obtain N-(2-thienylmethyl)-4-isopropylbenzamide. Yield: 80%.

EXAMPLE 7

Influence of reaction temperature on the yield:

Thiophene (25 mmol), acetaldehyde (20 mmol) and 4-isopropylbenzamide (10 mmol) were stirred in formic acid (10 ml) under the following condition to obtain N-[1-(2-thienyl)ethyl]-4-isopropylbenzamide:

Run 1

Reaction temperature and time: 60° C., 0.5 hr.
Yield: 45%.

Run 2

Reaction temperature and time: 50° C., 0.5 hr.
Yield: 55%.

Run 3

Reaction temperature and time: 40° C., 1.5 hrs.
Yield: 65%.

Run 4

Reaction temperature and time: 30° C., 2 hrs.
Yield: 76%

Run 5

Reaction temperature and time: 20° C., 3 hrs.
Yield: 74%.

Run 6

Reaction temperature and time: 13° C., 6 hrs.
Yield: 64%.

Run 7

Reaction temperature and time: 2° C., 6 hrs.
Yield: 56%.

EXAMPLE 8

Influence of the concentration of formic acid on the yield:

Thiophene (50 mmol), acetaldehyde (10 mmol) and 4-isopropylbenzamide (10mmol) were stirred in the following amount of formic acid at 20° C. for three hours to obtain N-[1-(2-thienyl)ethyl]-4-isopropylbenzamide:

Run 1

Formic acid: 10 ml.
Yield: 75%.

Run 2

Formic acid: 15 ml.
Yield: 78%.

EXAMPLE 9

Influence of the ratio of formic acid/phosphoric acid on the yield:

Thiophene (100 mmol), acetaldehyde (10 mmol) and 4-isopropylbenzamide (10 mmol) were stirred in the following formic acid/phosphoric acid mixture at 20° C. for two hours to obtain N-[1-(2-thienyl)ethyl]-4-isopropylbenzamide:

Run 1

Formic acid/phosphoric acid =9 ml/1 ml.
Yield: 86%.

Run 2

Formic acid/phosphoric acid =8 ml/2 ml.
Yield: 88%.

COMPARATIVE EXAMPLE 1

Thiophene (25 mmol), acetaldehyde (20 mmol) and 4-isopropylbenzamide (10 mmol) were stirred in acetic acid (10 ml) at 60° C. for 4.5 hours to obtain N-[1-(2-thienyl)ethyl]-4-isopropylbenzamide. Yield: 7%. This result means that a general method which uses acetic acid as a solvent gives the product in a low yield.

COMPARATIVE EXAMPLE 2

Thiophene (25 mmol), acetaldehyde (20 mmol) and 4-isopropylbenzamide (10 mmol) were stirred in a mixture of acetic acid/sulfuric acid (10 ml/0.2 ml) at 60° C. for one hour to obtain N-[1-(2-thienyl)ethyl]-4-isopropylbenzamide. Yield: 5%. A large part of the product was a tar-like material.

COMPARATIVE EXAMPLE 3

Thiophene (50 mmol), acetaldehyde (10 mmol) and 4-isopropylbenzamide (10 mmol) were stirred in a mixture of acetic acid/sulfuric acid in the following ratio at room temperature for two to three hours to obtain N-[1-(2-thienyl)ethyl]-4-isopropylbenzamide:

Run 1

Acetic acid/sulfuric acid =9 ml/1 ml.
Yield: 33%.
A large part of the product was a tar-like material.

Run 2

Acetic acid/sulfuric acid =10 ml/0.1 ml.
Yield: 20%.
A large part of the product was a tar-like material.

Run 3

Acetic acid/sulfuric acid =4 ml/1 ml.
Yield: 20%.
A large part of the product was a tar-like material.

Comparative Example 3 shows that the decomposition and the formation of tar occur when the acetic acid/sulfuric acid mixture is used.

COMPARATIVE EXAMPLE 4

Thiophene, acetaldehyde and 4-isopropylbenzamide were stirred in a mixture of acetic acid/concentrated hydrochloric acid in the following ratio under the following reaction condition to obtain N-[1-(2-thienyl)ethyl]-4-isopropylbenzamide. In Runs 1 and 2, a large part of the product was a tar-like material.

Run 1

Acetic acid/concentrated hydrochloric acid =10 ml/0.5 ml.
Thiophene/aldehyde/amide =25 mmol/20 mmol/10 mmol.
Reaction temperature: 60° C.
Reaction time: 1 hr.
Yield: 10%.

Run 2

Acetic acid/concentrated hydrochloric acid =9 ml/1 ml.
Thiophene/aldehyde/amide =50 mmol/10 mmol/10 mmol.
Reaction temperature: 20° C.
Reaction time: 3 hrs.
Yield: 50%.

Run 3

Acetic acid/concentrated hydrochloric acid = 10 ml/0.1 ml.

Thiophene/aldehyde/amide = 50 mmol/10 mmol/10 mmol.

Reaction temperature: 20° C.

Reaction time: 3 hrs.

Yield: 20%.

Runs 1 and 2 of Comparative Example 4 show that the decomposition and the formation of tar occur when the acetic acid/concentrated hydrochloric acid mixture is used.

What is claimed is:

1. A method of preparing an N-[1-(thienyl)alkyl]amine derivative of the formula:

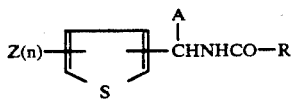   (I)

which comprises reacting a thiophene derivative of the formula:

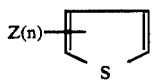

with an aldehyde of the formula:

ACHO and an amine of the formula:

NH$_2$—CO—R in the presence of formic acid or a mixture of formic acid and phosphoric acid,
wherein,
Z is a halogen atom, a lower alkyl group or a lower alkoxy group; (n) is 0, 1 or 2;
A is a hydrogen atom or an alkyl group having 1 to 8 carbon atoms;
R is a lower alkyl group, a group of the formula:

in which X and Y are the same or different and each a hydrogen atom, a straight or branched lower alkyl group (X and Y may form a ring,) a straight or branched lower haloalkyl group, a straight or branched lower alkoxy group, a straight or branched lower alkoxymethyl group or a halogen atom, or a group of the formula:

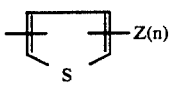

in which Z and (n) are the same ad defined above.

2. The method according to claim 1, wherein formic acid alone is used in an amount of 200 to 2000 ml per one mole of the amide.

3. The method according to claim 1, wherein the mixture of formic acid and phosphoric acid in a volume ratio of 1:1 to 10:1 is used in an amount of 200 to 2,000 ml per one mole of the amide.

4. The method according to claim 1, wherein the molar ratio of said amide to said aldehyde is from 1.0:3.0 to 1.0:1.0.

5. The method of claim 4, wherein said molar ratio is from 1.0:1.0 to 1.0:1.2.

6. The method according to claim 1, wherein the molar ratio of said amide to said thiophene derivative is from 1.0:1.0 to 1.0:20.

7. The method according to claim 6, wherein the molar ratio of said amide to said thiophene derivative is 1.0:5.0 to 1.0:10.

8. The method according to claim 1, wherein the reaction temperature is in the range from 0° to 50° C.

9. The method according to claim 8, wherein said reaction temperature is in the range from 20° to 30° C.

10. The method according to claim 1, wherein the reaction time is in the range from 30 minutes to 4 hours.

11. The method according to claim 1, wherein said thiophene derivative is thiophene, said aldehyde is paraldehyde, and said amide is 4-isopropylbenzamide.

12. The method according to claim 1, wherein said thiophene derivative is 2-bromothiophene, said aldehyde is paraldehyde, and said amide is 4-isopropylbenzamide.

13. The method according to claim 1, wherein said thiophene derivative is 3-bromothiophene, said aldehyde is paraldehyde, and said amide is 4-isopropylbenzamide.

14. The method according to claim 1, wherein said thiophene derivative is 2-ethylthiophene, said aldehyde is paraldehyde, and said amide is 4-isopropylbenzamide.

15. The method according to claim 1, wherein said thiophene derivative is thiophene, said aldehyde is paraldehyde, and said amide is acetamide.

16. The method according to claim 1, wherein said thiophene derivative is thiophene, said aldehyde is formaldehyde, and said amide is 4-isopropylbenzamide.

* * * * *